US00PP08395P

United States Patent [19]

Ross

[11] Patent Number: Plant 8,395

[45] Date of Patent: Sep. 28, 1993

[54] *AJUGA REPTANS* VARIETY NAMED 'ARCTIC FOX'

[76] Inventor: Henry A. Ross, 16711 Pearl Rd., Strongsville, Ohio 44136

[21] Appl. No.: 908,980

[22] Filed: Jul. 6, 1992

[51] Int. Cl.[5] ..... A01H 5/00
[52] U.S. Cl. ..... Plt./54.1
[58] Field of Search ..... Plt./54.1

[56] References Cited

U.S. PATENT DOCUMENTS

P.P. 1.492 7/1956 Corliss ..... Plt. 54.1
P.P. 7.619 8/1991 Turner ..... Plt. 54.1

*Primary Examiner*—James R. Feyrer
*Assistant Examiner*—Erich Veitenheimer

[57] ABSTRACT

*Ajuga reptans* mutation, named *Ajuga reptans* Variety 'Arctic Fox' which is of an absolutely unique coloration never before reported or described in Ajuga. It has leaves which are predominantly white or creamy-white; edged with a deep avacodo-green edging of varying width . . . with the green edging being ruffled, the degree of ruffling dependent upon the width of the green margin. Additionally . . . during cool periods of the year, the center of the leaf carries a mottled portion of silver-grey of varying size, lending an added enhancement to the already spectacular foliage effect.

1 Drawing Sheet

BACKGROUND AND SUMMARY

The present invention relates to a new and distinct variety (clone) of normal size; of *Ajuga reptans,* which was originated by me (at the Gardenview Horticultural Park in Strongsville, Ohio) from a spontaneous mutation which appeared as a sport on a plant of *Ajuga reptans* Variety 'Silver Queen'. The variety 'Silver Queen' itself originated as a mutation from the green-leaved wild type of *Ajuga reptans.*

The new variety, viz., *Ajuga reptans* Variety 'Arctic Fox' exhibits conspicuously variegated foliage leaves of a unique coloration which has never been observed or described before, I separated the tiny bit of sport from its parent plant and isolated it to be grown on separately. As new growth appeared; I removed any portion which did not exhibit the unique foliage coloration for which I had selected, and during constant culling over a period of five years; the plant was slowly transformed so that the entire plant showed the desired varigation. The major central portion of the leaf varies from white to various shades of creamy white . . . depending upon environmental conditions; except for the dark green marinal portions. The width of the green marginal portions varies, both between different leaves, as well as within each individual leaf. The margin may vary from no green at all, to a hairline of green to having a width equal to one quarter of the entire lamina, at the same transverse level of the lamina. In addition, a salient feature of the new variety is that, on those laminae of foliage leaves which develop during cool periods of the growing season; the median-longitudinal sector of the lamina, in adaxial view, appears silvery-green in color. This median-longitudinal sector may vary in diameter, both between foliage leaves and within a single foliage leaf. Also, within one leaf, the outline of this sector may appear irregular and asymmerical. In contrast, the laminae of the foliage leaves, developing during periods of hot periods of the growing season; this silvery-green color is usually absent or greatly reduced and, instead, the median-longitudinal region of lamina, in adaxial view; appears white or cream-colored; as described above.

BRIEF DESCRIPTION OF THE DRAWING

The top figure of the drawing shows complete, potted specimen in perspective, with inflorescence typical of the species.

The bottom figure, taken in a plan view of a specimen in a younger stage, shows the characteristic, haphazard forms of leaf variegation and lamination displayed by the plant.

BOTANICAL DESCRIPTION

On this variety of *Ajuga reptans* . . . as with the type species itself; the mature portions of stems exhibit a purple coloration, although the intensity and shade of the purple coloration is variable, varying from light purple to dark purple.

The petioles of the foliage leaves are winged and substantially variable in color. Depending upon environmental conditions and perhaps other factors . . . an entire petiole, in adaxial view, may be white or cream-colored, or it may be variegated to varying degrees, e.g. being cream-colored along the median and dark green along each margin. In addition, the petiole, in adaxial view, may exhibit various degrees of purple shading, again depending upon environmental conditions.

To date, flowering has been very sparse in my material with only three floweing spikes having been produced, which were not more than six inches in height . . . possibly because I have divided the plants intensively to increase my stock of plants. In the spikes that have been produced, over a five-year period; at least some of the flowers appeared variegated, i.e.: their corolas . . . in adaxial view . . . exhibiting patters like those described for the laminae of the foliage leaves. On many bracts, in adaxial view; the entire laminate appears cream-colored, except for the dark green marginal portions. Inflorescence of this plant is substantially like that of the species.

My new variety clearly differs from all other previously known varieties of *Ajuga reptans* because of the massive proportion of white or cream color within the foliage. No previously reported variety exhibits nearly this much white or cream color or this degree of type of variegation. It should be emphasized that these differences clearly distinguish *Ajuga reptans* Variety 'Arctic Fox', even from the parental variety, viz. *Ajuga reptans* variety 'Silver Queen', which has silvery-green foliage with only a few white, or creamy spots scattered over the leaf.

The leaves compromise, predominantly, three primary colors . . . each varying as to shade and intensity from leaf to leaf and even within the same leaf . . . usually a deep avacodo green (similar to Pantone 3308c,), which generally extends inwardly from the margins of the leaves to varying degrees . . . a white, or creamy white irregular zone between the outer zone and central zone; and a light silvery-greyish green (similar to Pantone Cool Grey 3-c) color which usually is expressed in central portions of those leaves which develop during cool periods of the growing season. The patterns formed are characteristically different from leaf to leaf and are thought to derive from two or more genetically distinct histogenic regions of the leaf forming meristem, and are thought to represent a periclinal type of chimera. The leaf cells formed from each region differ in chlorophyll content; resulting in differences in coloration and growth rate. Due to differences in speed of growth, the tissue formed by each respective region will develop into varied patterns relative to one another, giving different expressions in leaf mesophyll layers and the pallisade cell layer. This results in different patterns, determined by the area of each layer occupied by cells of each genotype. Where one or more layers of cells of silver or white overlay a layer of green cells, intermediate colors are displayed at the leaf surface and the leaf takes on a laminated appearance. Because more than one layer of mesophyll cells may develop from a different meristematic region; one, two or more layers of silver or white colored cells may mask the green of underlying cells of a lower cell layer, and the lamination may look several layers deep and result in two or more intermediate colors of different shades.

Although *Ajuga reptans* Variety 'Arctic Fox' has such a large proportion of white in its makeup; one would expect that it would grow more slowly than the green type but this has not been the case. The rate of growth is almost exactly the same as its parent *Ajuga reptans* Variety 'Silver Queen' and even the wild green type *Ajuga reptans. Ajuga reptans* Variety 'Arctic Fox' . . . at least in the northern Ohio area has grown equally well in sunny areas as in shady areas although, in areas of more sun, the plant tends to be lower growing and more compact than in shady areas where it is somewhat taller and looser growing. It is normally, and usually a lot mat of foliage borne flat on the ground.

In the northern Ohio Area, *Ajuga reptans* Variety 'Arctic Fox' has been practically deciduous with the foliage dying back almost to the central crown of the plant, usually about mid-December. It begins to grow sometime in March and usually blooms sometime in May. To date, no seeds have been produced although . . . since it has only produced three flower spikes to date, that does not necessarily mean that it is sterile. Plants carried over winter in a warm greenhouse have been evergreen, suggesting that . . . in milder climates . . . it will be evergreen.

*Ajuga reptans* Variety 'Arctic Fox' has not exhibited any disease or insect damage to date.

Except for the unique coloration described above: *Ajuga reptans* Variety 'Arctic Fox' is botanically identical with the wild type *Ajuga reptans* which is described as follows *A. reptans* Rhizomatous perennial with long stolons; stems 10–40 cm, pubescent on opposite faces, alternating at each node, sometimes glabrous at the base. Lower leaves 25–90×10–40 mm, ovate, entire or crenate. Bracts ovate, often tinged with blue, the upper shorter than the flowers. Vertillasters crowded, usually 6-flowered. Calyx 14–1;7 mm blue, rarely pink or white; tube exceeding calyx; upper lip entire. Stamens exserted; filaments hairy, $2n=32$.

I have propagated *Ajuga reptans* Variety 'Arctic Fox' vegetatively . . . by division . . . at the Gardenview Horticultural Park in Strongsville, Ohio, of which I am the Founder and Director. The resulting plants have been true to type except for the natural variation caused by environmental conditions and the different rates of growth between the green and non-green portions of the plant; as described above. *Ajuga reptans* Variety 'Arctic Fox' has been custom-propagated for me by tissue culture at the Briggs Nursery in Oregon (which produces 950 plants) and has come substantially true to type but this does not mean that it can just be planted out and ignored. If that is done, it will revert to plain green in just a year or two. With careful culling, the unique variagation can be easily maintained.

As a positive means of identification, pressed Herbarium specimens are being prepared and . . . along with colored photographs; will be deposited with the Herbarium at Cleveland State University, with the Bailey Hortorium and with the Royal Botanic Gardens-Kew.

I claim:

1. A new and distinct variety of *Ajuga reptan* named 'Arctic Fox' substantially as described and illustrated.

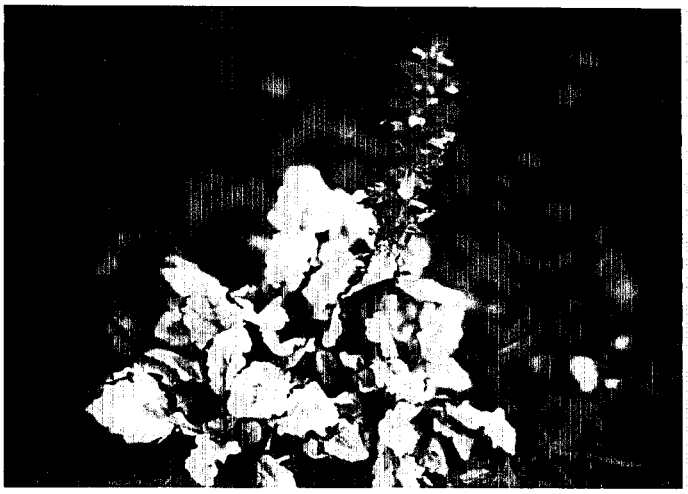
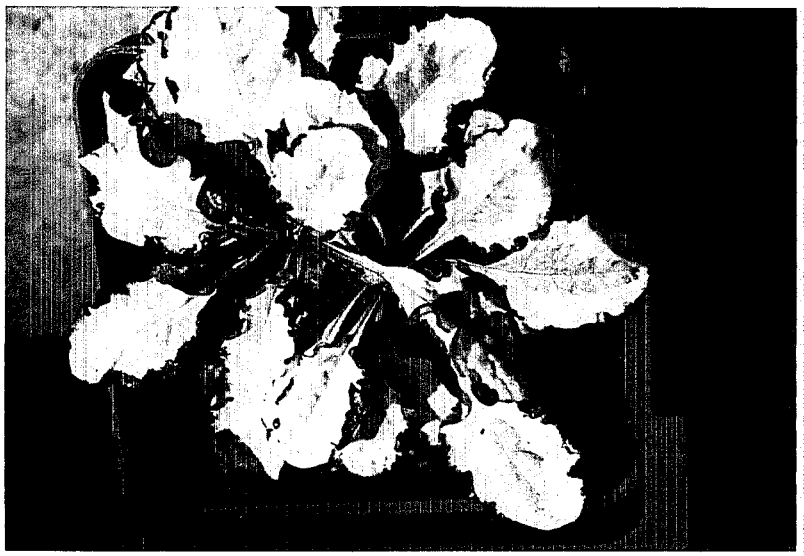

* * * * *